United States Patent
Bertin et al.

(10) Patent No.: US 10,345,424 B2
(45) Date of Patent: Jul. 9, 2019

(54) DETECTION UNIT AND METHOD FOR IDENTIFYING AND MONITORING CLOUDS IN AN OBSERVED AREA OF THE SKY

(71) Applicant: REUNIWATT, Saint Denis (FR)

(72) Inventors: Clement Bertin, Fonroque (FR); Sylvain Cros, Paris (FR); Nicolas Schmutz, Hoenheim (FR); Olivier Liandrat, Neffes (FR); Nicolas Sebastien, Saint Denis (FR); Samuel Lalire, Saint Pierre (FR)

(73) Assignee: REUNIWATT (FR)

( * ) Notice: Subject to any disclaimer, the term of this patent is extended or adjusted under 35 U.S.C. 154(b) by 0 days.

(21) Appl. No.: 15/513,617

(22) PCT Filed: Sep. 24, 2015

(86) PCT No.: PCT/EP2015/071959
§ 371 (c)(1),
(2) Date: Mar. 23, 2017

(87) PCT Pub. No.: WO2016/046309
PCT Pub. Date: Mar. 31, 2016

(65) Prior Publication Data
US 2017/0299686 A1 Oct. 19, 2017

(30) Foreign Application Priority Data
Sep. 26, 2014 (FR) ....................................... 14 59124

(51) Int. Cl.
*G01J 5/00* (2006.01)
*G01S 3/786* (2006.01)
(Continued)

(52) U.S. Cl.
CPC .............. *G01S 3/786* (2013.01); *G01C 5/00* (2013.01); *G01J 5/0014* (2013.01); *G01J 5/025* (2013.01);
(Continued)

(58) Field of Classification Search
CPC .......... G01S 3/786; G01C 5/00; G01J 5/0014; G01J 5/025; G01N 19/10; H04W 4/005
See application file for complete search history.

(56) References Cited

U.S. PATENT DOCUMENTS

| | | | |
|---|---|---|---|
| 4,171,911 A | 10/1979 | Aberle et al. | |
| 2006/0214843 A1* | 9/2006 | Klein | G01K 11/006 342/351 |
| 2016/0187535 A1* | 6/2016 | Maschhoff | G01W 1/10 250/338.5 |

FOREIGN PATENT DOCUMENTS

| | | |
|---|---|---|
| FR | 2363790 | 3/1978 |
| WO | 2013124432 | 8/2013 |

OTHER PUBLICATIONS

Smith et al., Measuring Cloud Cover and Brightness Temperature with a Ground-Based Thermal Infrared Camera, Feb. 2008, American Meteorological Society, vol. 47, pp. 683-693.*
(Continued)

*Primary Examiner* — Christine S. Kim
(74) *Attorney, Agent, or Firm* — Perman & Green, LLP

(57) ABSTRACT

A detecting assembly and method for identifying and tracking clouds in a zone of the sky being observed where some thermal-infrared flux emitted by the zone is collected and transmitted to a thermal-infrared detector, the detector including a sensor sensitive to the flux in a set band of wavelengths, a measurement of the actual temperature and actual relative humidity of the air at ground level is carried out and the vertical temperature and water vapor distribution is deduced therefrom, the dataset relating to the thermal-
(Continued)

infrared signal emitted by a reference sky for the vertical temperature and water vapor distribution is stimulated or obtained, the dataset thus simulated or obtained is subtracted from the dataset measured by the sensor to determine if clouds are present in the zone, and the dataset thus obtained is processed in order to compute the optical thickness and/or altitude of each cloud in the observation area.

14 Claims, 3 Drawing Sheets

(51) Int. Cl.
*G01W 1/10* (2006.01)
*G01W 1/12* (2006.01)
*G01C 5/00* (2006.01)
*G01J 5/02* (2006.01)
*G01N 19/10* (2006.01)
*H04W 4/70* (2018.01)

(52) U.S. Cl.
CPC .............. *G01N 19/10* (2013.01); *G01W 1/10* (2013.01); *G01W 1/12* (2013.01); *H04W 4/70* (2018.02)

(56) References Cited

OTHER PUBLICATIONS

International Search Report, International Application No. PCT/EP2015/071959, dated Dec. 4, 2015.

Nugent, et al. "Infrared Cloud Imaging in Support of Earth-space Optical Communication", Optics Express, vol. 17, No. 10, 2009, pp. 7862-7872.

* cited by examiner

DETECTION UNIT AND METHOD FOR IDENTIFYING AND MONITORING CLOUDS IN AN OBSERVED AREA OF THE SKY

CROSS-REFERENCE TO RELATED APPLICATIONS

This application is the National Stage of International Application No. PCT/EP2015/071959, having an International Filing Date of 24 Sep. 2015, which designated the United States of America, and which International Application was published under PCI Article 21 (2) as WO Publication No. 2016/046309 A1, and which claims priority from and the benefit of French Application No. 1459124, filed on 26 Sep. 2014, the disclosures of which are incorporated herein by reference in their entirety.

BACKGROUND

1. Field

The presently disclosed embodiment relates to a detecting assembly and method for identifying, in particular by estimation, physical properties of clouds, and for tracking one or more clouds in a zone of the sky, which zone is placed under observation from the ground.

The presently disclosed embodiment also relates to a method permitting actual metrological conditions to be determined and short-term metrological predictions to be made.

2. Brief Description of Related Developments

Sky cover is conventionally evaluated by a human observer from the ground. The horizon line that the observer sees under a certain solid angle defines the celestial dome for which this observer will evaluate the estimated sky cover.

Purely by way of illustration, when the sky is said to be covered, i.e. completely cloudy, its estimated sky cover is equal to 8 oktas. The unit for measuring sky cover, i.e. the okta, therefore corresponds to one eighth of the celestial dome.

However, the empirical character of this estimation is incompatible with the increasingly strict reliability and precision requirements demanded in certain present-day fields of activity.

By way of illustration, in the aeronautical field, the pilot of an aircraft must have precise knowledge of the metrological conditions, and in particular of the sky cover, around an airport in order to land or take off.

Likewise, the electricity production generated by a photovoltaic power plant may be qualified intermittent because it will depend strongly on climatic variables, in particular sky cover.

Specifically, the shadow of a cloud may come to fall at least partially on the photovoltaic panels of this plant, thus leading to a decrease in the amount of electricity generated.

In order to maintain the stability of the mains grid, the grid operator must then implement grid stability tools to compensate for any decrease in the production of electricity of photovoltaic origin.

By way of example, these stability tools may be simple batteries that discharge their power to the electrical grid in case of a momentary expected decrease in electricity generation, or gas turbines in case of a long expected decrease in electricity generation.

However, the implementation of these stability tools is not optimized at the present time, due to the lack of a precise and reliable tool for predicting the amount of electricity of photovoltaic origin that will be generated.

This lack of data generates direct costs (fuel consumed, plant aging) and indirect costs, such as the generation of carbon dioxide ($CO_2$) in the case of untimely turn on.

Nevertheless, photovoltaic power remains an inexhaustible and relatively clean energy source. The number of photovoltaic power plants in operation has therefore seen substantial growth and will continue to grow over the next few years.

Technical solutions aiming to identify and track clouds in a region of the sky have been proposed over the last few years.

Thus, infrared video cameras have been used to record the infrared emission of clouds in order to determine therefrom certain characteristics such as temperature. From the latter, the altitude of the corresponding cloud may be deduced.

However, it has been observed that these measurements cannot be relied upon because they do not take into account the contribution of the atmosphere located between the infrared video camera and the one or more clouds thus measured.

Yet, the contribution of this intermediate atmosphere may prove to be large in certain wavelength ranges of interest.

There is therefore a pressing need for a detecting assembly and method allowing the contribution of the atmosphere located between the detector and the one or more clouds to be subtracted, in order to precisely identify one or more clouds in a zone of the sky observed from the ground, and to track each thereof.

The objective of the presently disclosed embodiment is therefore to provide a detecting method and assembly for identifying and tracking from the ground one or more clouds in a given region of observation of the sky, this method and assembly being simple in their design and in their operating mode, reliable and precise.

Another objective of the presently disclosed embodiment is to provide a detecting assembly such as this that is able to operate night and day and that is robust and easy to maintain and therefore inexpensive. Such a detecting assembly will thus advantageously be able to operate automatically in out of the way zones.

Yet another objective of the presently disclosed embodiment to provide a method for making short-term predictions, for example of a time t+30 minutes ahead, allowing the attenuation to come of the insolation of photovoltaic panels resulting from a shadowing effect caused by one or more clouds progressing toward a photovoltaic power plant to be determined with a high degree of exactness.

Such a method would allow a mains grid operator to obtain reliable information on the level of photovoltaic electricity generation to be expected over the short term, and therefore to more easily manage grid stability tools.

SUMMARY

Thus, the disclosed embodiment relates to a detecting method for identifying and tracking one or more clouds in a zone of the sky, said zone being observed from the ground.

According to the disclosed embodiment, the following steps are carried out:

a step in which at least some of the thermal infrared flux emitted by said observed zone of the sky is collected and transmitted to at least one thermal infrared detector, said at least one thermal infrared detector including at least one sensor that is sensitive to said flux in a set band of wavelengths;

a step in which at least one measurement of the actual temperature and actual relative humidity of the air at ground level is carried out and the vertical temperature and water-vapor distribution is deduced therefrom;

a step in which the dataset relating to the thermal infrared signal emitted by a reference sky for said vertical temperature and water-vapor distribution thus deduced is simulated or obtained;

a step in which the dataset thus simulated or obtained is subtracted from the dataset measured by said at least one sensor so as to determine whether or not one or more clouds are present in said zone of observation of the sky; and a step in which the dataset thus obtained is processed in order to compute the optical thickness and/or altitude of each cloud in said observation of the sky.

The expression "the ground" is understood to mean the surface of the ground, said surface possibly having a positive or negative altitude with respect to sea-level, or a portion, such as the top, of a construction or dwelling, a multistory building for example. The method of the presently disclosed embodiment therefore does not relate to measuring devices installed on board a vehicle, an aircraft or a satellite for example.

The evolution of the shadow of a cloud on the ground depends on its altitude, just as its impact on the radiation depends on its optical thickness.

The present detecting method advantageously allows the precision of predictions to be improved by determining the optical thickness and altitude of each cloud in the observed zone of sky after subtraction of the contribution of the atmosphere from the measurements actually taken.

Since the atmospheric radiation depends on the precipitable water vapor column (PWVC=Wp) and the temperature on the ground (expressed in upward flux, Ls), the affine correlation function may be written:

$$L_{sky} = A \times L_S \times W_p + B \times W_p + C \times L_c + D$$

The precipitable water vapor column is measurable by radiosonde or estimatable using the Reitan relationship:

$$Ln(W_p) = a \times T_{dew} + b$$

A set of thresholds is determined to segment the thermal images as a function of $\Delta Tb$, the difference in brightness temperature between a reference sky and each cloud. These thresholds are estimated on the basis of technical characteristics of the thermal infrared detector.

Advantageously, the reference sky is a zone of clear sky. Preferably, datasets relating to the thermal infrared signal emitted by this reference sky for different vertical temperature and water-vapor distributions are stored in a storage unit. It is thus possible to easily access these datasets and to load a dataset corresponding to the vertical temperature and water-vapor distribution deduced in step b).

Alternatively, such datasets may be simulated, or even computed, by processing means including a computational unit such as a computer.

Moreover, the present method allows, on the basis of measurements actually taken at ground level, the vertical temperature and water-vapor distribution to be deduced.

These measurements of the temperature on the ground and of the humidity of the air at ground level thus advantageously allow knowledge of the vertical variation in temperature and water vapor typically obtained by auxiliary means that are complex to implement to be replaced. Purely by way of illustration, the vertical distribution is generally derivable from satellite data or even from data obtained by weather balloon.

This deduction of the vertical temperature and water-vapor distribution at a given place from measurements actually taken at ground level has the required reliability. It is carried out on the basis of known data, such as atmospheric profiles modelled beforehand, these profiles being generated from data obtained by satellite and weather balloon, and being averaged by season and climatic zone; these data are recorded in a storage unit, and are accessible to the processing means comprising a computational unit such as a computer, on which a suitable data-processing software package is installed.

In various particular aspects of this method, each of which has its own particular advantages and which are combinable in many technically possible combinations:

prior to step a), said at least one sensor of said thermal infrared detector is calibrated using a single reference surface at ambient temperature.

It may be a question of a black shield placed in front of the thermal infrared detector. The offset is calculated with the temperature of the shutter, which temperature is measured using, a thermometer.

The dataset-processing step e) comprises a step of inverting the radiative transfer model, allowing the horizontal spatial distribution of the optical thickness and/or altitude of the single cloud layer or of all the clouds in said observation zone of the sky to be determined.

Preferably, to compute the optical thickness of each cloud at the wavelengths of interest, the cloud model is determined beforehand and the radiation emitted by each cloud is simulated depending on the cloud model thus determined.

The ground measurements delivered by said at least one thermometer and said at least one hygrometer allow said processing means to converge on an ideal solution via a processing step based on a software package ensuring the radiative transfer model inversion.

Specifically, the vertical temperature and water-vapor profiles deduced from the ground measurements in step b) are known elements of the metrological situation. The unknown elements are the altitude and/or optical thickness of the clouds. The inversion of the model consists in seeking the ideal solution (altitude/optical thickness pair) minimizing the difference between the thermal infrared radiation simulated by the radiative transfer model and that measured by the sensor. To do this, the software package performing the inversion varies the values of the (altitude/optical thickness) pair keeping the values of the vertical temperature/water-vapor profiles constant. Thus, by virtue of the temperature and water-vapor measurements, the processing means allow the ideal solution to be converged upon.

An optical sensor defining a zone of observation of the sky from the around of at least 4.6 steradians is used to determine, from the texture and color of each cloud detected by said optical sensor, the corresponding type of cloud and to deduce therefrom a range of altitudes of each cloud present in said zone of observation of the sky.

This optical sensor permits the software package for processing the datasets to learn beforehand the types of cloud liable to be detected in the zone of observation of the sky, which zone is dependent on the site of installation of the detecting assembly. Thus the data-processing step e) is facilitated.

Preferably, the zone of observation of the sky of at least 4.6 steradians is obtained by virtue of an optical sensor including a fisheye objective. Advantageously, this fisheye objective will have a field width at least equal to 150°. Purely by way of illustration, this objective will possibly be a circular fisheye objective having a coverage of 180° in all directions, thus giving a circularly bounded image.

Another aspect of the presently disclosed embodiment is a detecting assembly for implementing the method for identifying and tracking one or more clouds in a zone of the sky such as described above, said zone being observed from the ground, this assembly comprising:

a mirror having a conical or convex curved mirror surface, the surface of said mirror being turned toward at least one thermal infrared detector in order to collect at least some of the thermal infrared flux emitted by said observed zone of the sky and to redirect it toward said at least one thermal infrared detector, said at least one thermal infrared detector including at least one sensor that is sensitive to said flux in a set band of wavelengths, each sensor emitting measurement signals;

means for processing the signals emitted by said one or more sensors; and at least one thermometer and at least one hygrometer for measuring the actual temperature and actual relative humidity of the air at ground level and being connected to said processing means, and said processing means allowing, from these measurements, the vertical temperature and water-vapor distribution to be determined in order to correct for the contribution of the atmosphere between said assembly and the one or more clouds.

This detecting assembly, which is intended to be placed on the around, is advantageously able to operate both day and night. Night-time detection permits the evolution of the cloud ceiling to be tracked before dawn and thus the evolution in the first daylight hours to be predicted.

The convex curved mirror surface may thus be a mirror surface that is spherically, elliptically or parabolically convex in shape. A conical mirror surface advantageously allows detection at very high zenith angles, for example comprised between 60° and 90°, to be improved.

Preferably, said at least one thermometer and said at least one hygrometer comprise wireless communication means in order to address their measurements to said processing means or to a storage unit recording said data, said storage unit being connected to said processing means.

In various particular aspects of the disclosed embodiment of this detecting assembly, each of which has its own particular advantages and which are combinable in many technically possible combinations:

said at least one thermal infrared detector includes a plurality of elements that are sensitive to infrared radiation, said sensitive elements being microbolometers arranged in a matrix array.

Such a thermal infrared detector with automatic calibration, for example with respect to a reference surface at ambient temperature, makes the present assembly economical and rapidly implementable in that no prior calibration with black bodies is required.

Furthermore, since the sensitive elements do not require a cooling system, the assembly is very simple to use and may operate entirely autonomously.

The assembly includes a filter wheel including at least two distinct filters.

Each filter allows the thermal infrared flux received by said detector to be filtered selectively before this flux is received by said at least one sensor of said thermal infrared detector.

Preferably, this thermal infrared detector includes a storage unit including data relating to the filters and to one or more target objects in the sky, which objects are measured by means of each filter; and data allowing the filter of said wheel to select for the measurement of a particular target object in the sky to be identified. The latter data may be addressed to an element for moving said filter wheel so that the processing means addressing a control signal to this moving element, said filter wheel is moved by this moving element so that a suitable filter is positioned for the measurement of said target object in the observed zone of sky.

Likewise, the storage unit nay include a dataset relating to how to configure the thermal infrared detector depending on the selected filter of said wheel.

At least said signals emitted by said one or more sensors are wireless communication signals, said processing means including receiving means for receiving said wireless communication signals emitted by said one or more sensors.

These wireless communication signals may be based on the following protocols: IEEE 802.11 b/g/n (Wi-Fi), IEEE 802.15.1 (Bluetooth), IEEE 802.16 (WiMax), ZigBee IEEE 802.15.4 or even GSM or GPRS.

Of course, said processing means may include means for emitting and receiving wireless communication signals.

D being the distance separating said at least one detector from said mirror and A being the angular aperture of said at least one detector, said mirror has a radius R at least equal to $D \times \tan(A/2)$.

For a given small bulk, the resolution of the detecting assembly is thus significantly improved.

Said assembly comprises means for communicating over a GSM/GPRS/UMTS mobile network, a fixed-line network or even over a Wi-Fi wireless communication network in order to collect data, such as metrological data relating to the deployment site of said assembly, and/or to transmit data (such as images or measurements) relating to the results obtained by said processing means.

Preferably, this assembly also comprises a storage unit for recording therein said data, said storage unit being connected to said processing means so that the latter can access these data and, optionally, store therein other data.

Preferably, said assembly includes a photometer and a lidar or radar measuring system, in order to obtain complementary data that will be used in the determination of the properties of the one or more clouds present in said observed zone of the sky.

The presently disclosed embodiment also relates to a method for predicting the position of one or more clouds in the sky.

According to the disclosed embodiment, the movement and evolution at a time $t+\Delta t$ of each of the clouds in said zone of observation is determined from the dataset obtained at a time t, which dataset is obtained by the method for identifying and tracking one or more clouds in a zone of the sky such as described above, said zone being observed from the ground.

Purely by way of illustration, this estimation of the movement of the clouds is carried out on the basis of images of the observed zone of the sky, said images being obtained consecutively using the thermal infrared detector, and of an "optical flow" image-processing method, which is used to detect the movement of a cloud in this zone.

The presently disclosed embodiment is applicable to various technical fields:

airborne surveillance: automatic surveillance of the state of the sky;

determination or prediction of time windows favorable for laser communication between a satellite and an optical communication reception terminal;

reception by a terminal integrated into a vehicle, an aircraft for example, of signals originating from the ground;

astronomy.

BRIEF DESCRIPTION OF THE DRAWINGS

Other advantages, aims and particular features of the presently disclosed embodiment will become more clearly apparent from the following description, which is completely nonlimiting, intended as explanatory and given with reference to the appended drawings, in which.

DETAILED DESCRIPTION

Firstly it will be noted that the figures are not to scale.

Figure 1:
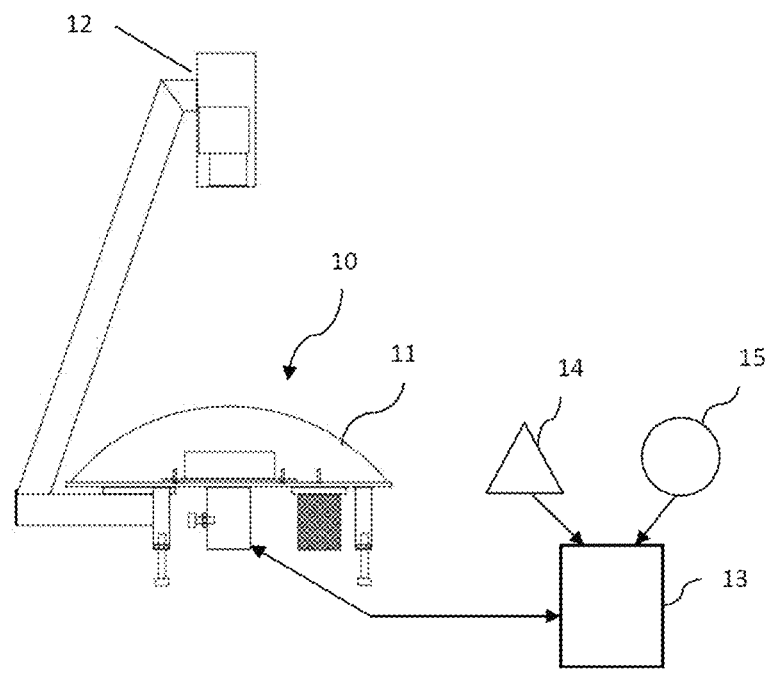
FIG. 1 schematically shows a detecting assembly for characterizing and tracking clouds in a zone of the sky according to one particular aspect of the presently disclosed embodiment, said zone being observed from the around.
Figure 2:
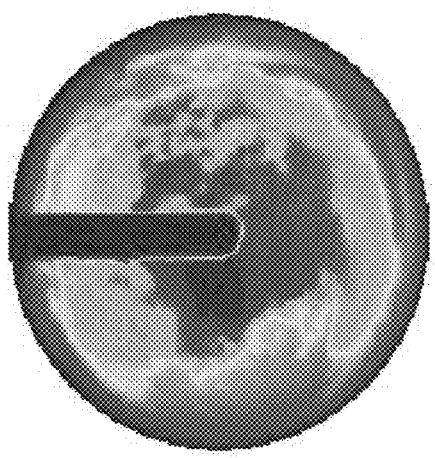
FIG. 2 shows a raw image obtained with the detection assembly in FIG. 1.

FIG. 1 shows a detecting assembly for characterizing and tracking clouds in a zone of the sky according to one particular aspect of the presently disclosed embodiment, said zone being observed from the ground.

The detecting assembly comprises a mirror 10 having a curved spherical mirror surface 11.

The mirror surface 11 is oriented toward a thermal infrared video camera 12 placed on the optical axis of this mirror at a distance d from this mirror surface 11, thus ensuring the compactness of the detecting assembly.

Advantageously, the angular aperture of the thermal infrared video camera 12 here being equal to 62° and the distance d separating this video camera 12 from the mirror 10 being 0.3 m in order to preserve the compactness of the assembly, the diameter of the spherical mirror is 0.36 m.

The surface of this mirror 11 ensures the collection of at least some of the thermal infrared flux emitted by the zone of the sky and redirects the collected flux toward the thermal infrared video camera 12, said zone being observed from the ground.

This thermal infrared video camera 12 includes sensors (not shown) that are sensitive to this thermal infrared flux in a set band of wavelengths, each sensor emitting measurement signals. Advantageously, these sensors are here microbolometers arranged in a matrix array.

The convex spherical mirror 10 is coated with an optical coating that is reflective in a band of wavelengths that is appropriate for the infrared measurement with the thermal infrared video camera 12.

By way of example, this optical coating is reflective at least in the band of wavelengths in which the sensors of the video camera are sensitive, for example between 7.5 and 14 microns, and even better between 9 and 14 microns.

The assembly also includes means 13 for processing the signals emitted by the sensors. These processing means 13 here comprise computer on which or more data-processing software packages are executed in order to process the signals received from the sensors, to store them and/or to transmit them to a remote location via a communication means.

The assembly also includes a thermometer 14 and a hygrometer 15 that are placed in immediate proximity to the mirror 10 in order to measure the actual temperature and actual relative humidity of the air at ground level. These two instruments are also connected to said processing means 13, which receive the signals emitted by these instruments in order to store them and process them.

The processing means 13 allow, from these actual measurements carried out at ground level, the vertical temperature and water-vapor distribution that will serve to correct for the contribution of the atmosphere between said assembly and the one or more clouds, to be determined.

FIGS. 2 to 6 show an exemplary measurement carried out with the detecting assembly described above.

Although it gives good results, correcting for the contribution of the atmosphere with a reference sky such as a clear sky may be further improved using an adaptive correction that allows the correct zenith temperature to be determined depending on the actual situation (cloudy or clear sky):

$$T = (T_h - a) \times (\theta/90)^b + a$$

where Th is the horizon temperature (K), b an empirical gradient parameter, θ zenith angle (rad) and a zenith temperature (K).

The brightness temperature a describes the state of the cloud in terms of altitude and optical thickness at the zenith in question.

The minimum temperature is that of clear sky (no clouds), and the maximum temperature is that of the lowest and most opaque cloud. All the intermediate temperatures correspond to other altitude/optical-thickness pairs.

This correction allows the equivalent brightness temperature at a given zenith angle to be determined.

Figure 3:
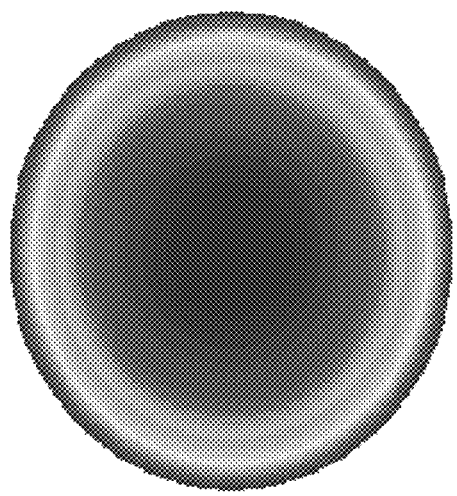
FIG. 3 shows the thermal infrared signal emitted by a clear sky for a vertical temperature and water-vapor distribution determined from actual measurements taken with the thermometer and hygrometer of the assembly in FIG. 1.
Figure 4:
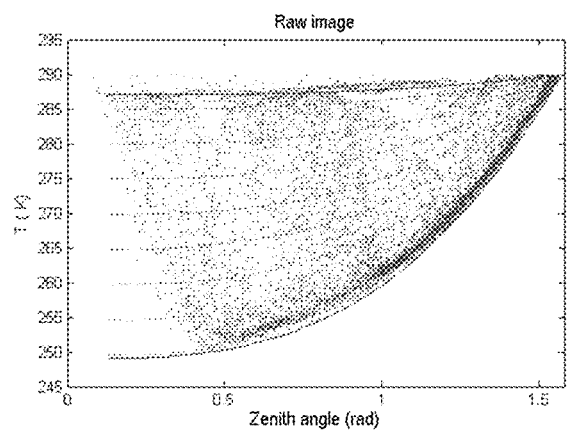
FIG. 4 shows, on the basis of a large number of brightness-temperature measurements, the empirical determination of brightness-temperature gradients as a function of zenith angle, for various classes of brightness temperature.

FIG. 4 shows, on the basis of a large number of brightness-temperature measurements (one measurement is represented by one dot), the empirical determination of brightness-temperature gradients (thermal infrared signal) as a function of zenith angle, for various classes of brightness temperature. This gradient is visible in the case of clear sky as FIG. 3 shows.

For each pixel of the image, the following steps are carried out:

a step in which a reference gradient is calculated for each zenith brightness temperature of the vector a, and a step in which the pixel is compared to the reference gradients (dashed curves in FIG. 4, the x-axis representing zenith angle (rad) and the y-axis representing temperature (K)).

The pixel that will be used for the correction is the zenith brightness temperature of the closest gradient.

Figure 5:
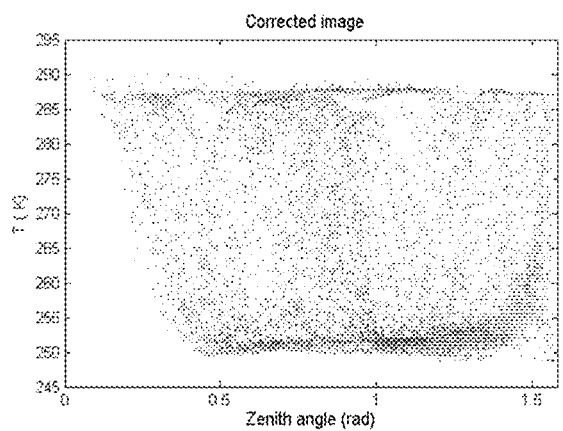
FIG. 5 shows the equivalent brightness temperatures at zenith a for the image shown in FIG. 2.

Once the model corresponds to the information contained in the image, it is possible to determine the equivalent zenith brightness temperatures a for all the image (FIG. 5, the x-axis representing zenith angle (rad), the y-axis representing temperature (K)).

Figure 6:
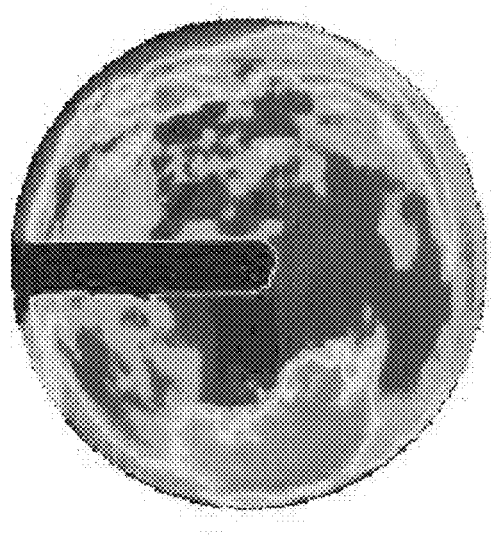
FIG. 6 shows an image of the zone of the sky, said zone being observed from the ground, said image having been corrected on the basis of FIG. 3.

FIG. 6 shows the corrected image after processing.

As a variant, instead of obtaining the clear sky luminance by synthesizing the vertical temperature and humidity distribution and using these profiles as the input of the radiative transfer model, it is possible, in the context of the presently disclosed embodiment, to simulate every possible clear-sky luminance on the basis of a large number of profiles generated from available archived meteorological data. In the context of this variant, the correlation between the simulated luminances and the associated measured dew-point temperatures (measured in the same location and at the same time) is sought. An empirical (quadratic) relationship between dew-point temperature and clear-sky luminance is deduced therefrom.

The measuring means, implemented in the context of the method according to the presently disclosed embodiment, measure the temperature and humidity on the ground. The due-point temperature is deduced therefrom using the Magnus-Tetens formula. On the basis of the empirical relationship, the clear-sky luminance corresponding to this dew-point temperature is obtained.

In one aspect, the dataset-processing step e) comprises a step of inverting the radiative transfer model, allowing the horizontal spatial distribution of the optical thickness and/or altitude of the single cloud layer or of all of the clouds in said zone of observation of the sky to be determined. A cloud is said to be "thick" if the temperature of its base, perceived by the instrument, is higher than a threshold defined beforehand for a given point of the sky at a given time. Beforehand, for a given place, the luminance of any type of thick cloud (that is realistically expectable for a given season and given local conditions) is modelled by a radiative transfer model on the basis of the physical (at least the altitude and geometric thickness) and micro-physical (at least the diameter of the water or ice particles forming the cloud, the particle concentration and the optical thickness) properties of the clouds. The values of these properties are chosen so as to be realistic for a cloud with respect to the season, to the geographic place in question and to the metrological conditions of the time in question. This luminance is then determined for various altitudes. The luminance of the clear (uncloudy) atmosphere portion under the cloud is also modelled. In the context of the method according to the presently disclosed embodiment, a relationship is postulated between the luminance perceived by the measuring instrument and the luminances modelled for a thick cloud and the atmospheric layer located therebelow:

$$L_{instrument} = L\text{thick cloud} + L\text{clear sky under the cloud} = L\text{thick cloud} + x \cdot L\text{completely clear sky}$$

We assume that Lthick_cloud and x are independent of altitude.

The look-up table construction links for a given clear-sky luminance value:

altitude, the luminance perceived by the measuring instrument, x, the luminance of the atmosphere under the cloud and the luminance of the cloud. All the necessary look-up tables are constructed beforehand, at least one per realistically expectable clear-sky luminance value.

Once the measurement of the luminance perceived by the measuring instrument has been taken, the known clear-sky luminance value is used to choose the right look-up table and to deduce therefrom the altitude of the cloud.

When the sky is clear, the instrument implemented in the context of the method according to the presently disclosed embodiment may perceive a condensation trail left following the passage of an airplane (or contrail). If a contrail is perceived, consultation of public air-traffic data such as those available on www.flightradar24.com allows the altitude of the airplane that generated this contrail, and therefore the altitude of this observed cloud, to be known to within 30 cm (1 foot). The luminance of this artificial cloud perceived by the measuring instrument then allows a verified association between the luminance and altitude of the cloud to be deduced. This allows a calibration point to be established for high altitudes (about 12000 m). This thus provides additional information on the clouds observed in the same field of view or indeed in the hours that follow or that precede the passage of this airplane, assuming that the state of the atmosphere has not significantly modified the clear-sky luminance.

What is claimed is:

1. A detecting method for identifying and tracking one or more clouds in a zone of the sky, said zone of the sky being observed from the ground, characterized in that the following steps are carried out:
   a) a step in which at least some of the thermal infrared flux emitted by said zone of the sky being observed is collected and transmitted to at least one thermal infrared detector, said at least one thermal infrared detector including at least one sensor that is sensitive to said thermal infrared flux in a set band of wavelengths;
   b) a step in which at least one measurement of an actual temperature and actual relative humidity of air at ground level is carried out and a vertical temperature and water-vapor distribution is deduced therefrom;
   c) a step in which a dataset relating to a thermal infrared signal emitted by a reference sky for said vertical temperature and water-vapor distribution thus deduced is simulated or obtained;
   d) a step in which the dataset thus simulated or obtained is subtracted from another dataset measured by said at least one sensor so as to determine whether or not one or more clouds are present in said zone of the sky being observed; and
   e) a step in which the dataset thus simulated or obtained in step c) is processed in order to compute an optical thickness and/or altitude of each cloud in said zone of the sky being observed.

2. The method as claimed in claim 1, wherein, prior to step a), said at least one sensor of said thermal infrared detector is calibrated using a single reference surface at ambient temperature.

3. The method as claimed in claim 1, wherein the dataset-processing step e) comprises a step of inverting a radiative transfer model, allowing a horizontal spatial distribution of the optical thickness and/or altitude of a single cloud layer or of all the clouds in said zone of the sky being observed to be determined.

4. The method as claimed in claim 3, wherein to compute the optical thickness of each cloud at wavelengths of interest, a cloud model is simulated beforehand and a radiation emitted by each cloud is simulated depending on the cloud model thus determined.

5. The method as claimed in claim 1, wherein, the one or more clouds being substantially transparent, the vertical temperature and water-vapor distribution of a clear sky is used in the dataset-processing step e) to deduce the optical thickness and/or altitude of each cloud.

6. The method as claimed in claim 5, comprising a step of determining the altitude of a cloud by postulating a relationship between a luminance perceived by a measuring instrument, and a modelled luminances of a cloud and of an atmospheric layer located therebelow and by implementing lookup tables.

7. The method as claimed in claim 1, wherein an optical sensor defining a zone of observation of the sky from the ground of at least 4.6 steradians is used to determine, from a texture and color of each cloud detected by said optical sensor, a corresponding type of cloud in order to deduce therefrom a range of altitudes of each cloud present in said zone of observation of the sky.

8. The method as claimed in claim 1, comprising a step of establishing a calibration point by analyzing a condensation trail left following a passage of an airplane.

9. A method for predicting a position of one or more clouds in a zone of observation in the sky, wherein a movement and evolution at a time t+Δt of each of the clouds in said zone of observation is determined from a dataset obtained at a time t, which dataset is obtained by the method for identifying and tracking one or more clouds in a zone of the sky as claimed in claim 1, said zone of the sky being observed from the ground.

10. A detecting assembly for identifying and tracking one or more clouds in a zone of the sky, said zone of the sky being observed from the ground, said assembly comprising:
a mirror having a conical or convex curved mirror surface, the surface of said mirror being turned toward at least one thermal infrared detector in order to collect at least some of the thermal infrared flux emitted by said zone of the sky being observed and to redirect it toward said at least one thermal infrared detector;
said at least one thermal infrared detector including at least one sensor that is sensitive to said thermal infrared flux in a set band of wavelengths, each sensor emitting measurement signals;
means for processing the signals emitted by said at least one thermal infrared detector including at least one sensor that is sensitive to said thermal infrared flux in the set band of wavelengths;
at least one thermometer and at least one hygrometer for measuring an actual temperature and actual relative humidity of air at ground level and being connected to said processing means; and
said processing means allowing, from the actual temperature and actual relative humidity of the air measurements, a vertical temperature and water-vapor distribution to be determined in order to correct for a contribution of the atmosphere between said assembly and the one or more clouds.

11. The assembly as claimed in claim 10, wherein said at least one thermal infrared detector includes a plurality of elements that are sensitive to infrared radiation, said sensitive elements being microbolometers arranged in a matrix array.

12. The assembly as claimed in claim 10, wherein at least said signals emitted by said at least one thermal infrared detector including at least one sensor that is sensitive to said thermal infrared flux in the set band of wavelength are wireless communication signals, said processing means including receiving means for receiving said wireless communication signals emitted by said one or more sensors.

13. The assembly as claimed in claim 10, wherein D being the distance separating said at least one detector from said mirror and A being the angular aperture of said at least one detector, said mirror has a radius R at least equal to D×tan (A/2).

14. The assembly as claimed in claim 10, wherein said assembly further comprises means for communicating over a GSM/GPRS/UMTS mobile network, a fixed-line network or even over a Wi-Fi wireless communication network in order to collect metrological data relating to the deployment site of said assembly, and/or to transmit data relating to results obtained by said processing means.

* * * * *